| United States Patent [19] | [11] Patent Number: 5,017,689 |
| Hruby et al. | [45] Date of Patent: May 21, 1991 |

[54] DYNORPHIN ANALOGS SPECIFIC FOR KAPPA OPIOID RECEPTORS

[75] Inventors: Victor Hruby; Andrew Kawasaki, both of Tucson, Ariz.

[73] Assignee: Arizona Technology Development Corporation, Tuscon, Ariz.

[21] Appl. No.: 375,882

[22] Filed: Jul. 6, 1989

[51] Int. Cl.$^5$ ............................ C07K 7/12; C07K 7/06
[52] U.S. Cl. .................... 530/327; 530/302; 530/317; 514/809
[58] Field of Search ............... 530/327, 302, 317; 514/11, 14, 15, 809

[56] References Cited

U.S. PATENT DOCUMENTS 4,148,786  4/1979  Sarantakis ..................... 530/330
4,518,711  5/1985  Hruby et al. .................... 514/11
4,684,620  8/1987  Hruby et al. .................... 514/11

OTHER PUBLICATIONS

Civelli et al., Proc. Natl. Acad. Sci., U.S.A., vol. 82, 1985, pp. 4291-4295.

*Primary Examiner*—Lester L. Lee
*Assistant Examiner*—Avis M. Davenport
*Attorney, Agent, or Firm*—Oblon, Spivak, McClelland, Maier & Neustadt

[57] ABSTRACT

Cyclic disulfide and linear dynorphin Dyn $A_{1-11}$ and dynorphin Dyn $A_{1-13}$ analogs which are highly specific for κ opioid receptors. These analogs are useful in pharmaceutical compositions and for the analysis of opioid receptor/ligand interactions.

13 Claims, 1 Drawing Sheet

U-50488  U-69593

U-62066

DYNORPHIN ANALOGS SPECIFIC FOR KAPPA OPIOID RECEPTORS

BACKGROUND OF THE INVENTION

1. Field of the Invention

The invention is directed to dynorphin oligopeptides with highly selective binding and biological activity at opioid receptors. More specifically, the invention is directed to cyclic and linear dynorphin A analogs which are highly potent and selective for kappa opioid receptors.

2. Discussion of the Background

Numerous oligopeptides have been identified in the central and peripheral nervous system. These oligopeptides display a variety of biological and pharmacological activities including analgesia, physiological dependence and tolerance, gut motility, etc. These nervous system oligopeptides include the highly active endorphins and enkephalns. Since the discovery of endogenous enkephalins there has been substantial research into the structure and activities of opioid oligopeptides and opioid non-peptides.

It is now well known that there are a multiplicity of opioid receptors in mammals, including the mu ($\mu$), delta ($\delta$), kappa ($\kappa$) and possibly other subtypes of these receptors. These different receptors are thought to have different physiological roles and to interact differently with the various brain oligopeptides A continuing goal of research into opioid receptors and brain oligopeptides is the discovery of oligopeptide ligands which are highly specific for only one type of opioid receptor and which exhibit highly specific biological and pharmacological activity. Such peptides contribute substantially to the understanding of opioid receptors and have important biological and medical applications, including the management of pain without the undesirable side effects of morphine and other narcotics.

The enkephalins such as H—Tyr—Gly—Gly—Phe—Met—OH, i.e., Met$^5$-enkephalin, have modest selectivities for the $\delta$ receptor, while the dynorphins such as dynorphinl-$_{1-11}$ (H—Tyr—Gly—Gly—Phe—Leu—Arg—Arg—Ile—Arg—Pro—Lys—OH) have modest specificity for the kappa receptor. The specificity of the various brain polypeptides for the individual receptors is thought to relate to the conformation and structure of the oligopeptides.

Shortly after the characterization of the endogenous enkephalins, attempts were made to determine their preferred conformations. By the use of various spectroscopic methods, such as X-ray crystallography and/or energy calculations, varying conclusions were reached. It is now accepted that the enkephalins are highly flexible molecules that can assume an ensemble of energetically preferred conformations.

There may be definite advantages for a biological system to utilize hormones or neurotransmitters having high conformational flexibility. Such advantages include the ability to utilize a variety of thermodynamically accessible pathways to ligand-receptor interactions, the ability of a specific hormone or neurotransmitter to assume different conformations, whereby the hormone or neurotransmitter could then effect different molecular pharmacological events, and the availability of different conformations for a specific ligand to permit binding to multiple types of receptors. For example, a single oligopeptide may variously bind to each of the mu, delta and kappa receptors with different specificity. Indeed, it is thought that the complexity of the pharmacological responses to the opioids may be due in part to their non-selective binding to opioid receptors.

In comparison to the mu and delta opioid receptors, research directed to kappa receptor oligopeptides has been limited, especially with peptide ligands. Structure-function studies have been primarily directed to the putative endogenous oligopeptides dynorphin A (Dyn A), dynorphin B (Dyn B) and α-neoendorphin.

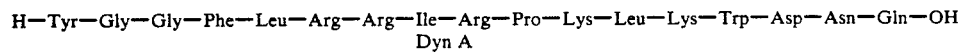
Dyn A

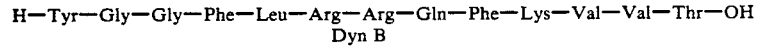
Dyn B

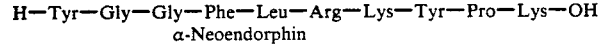
α-Neoendorphin

Some structure-function relationships for dynorphin peptides have been determined (see for example, Chavkin, C.; Goldstein, A. (1981) Proc. Natl. Acad. Sci., USA 78, 6543-6547; Lemaire, S., Lafrance, L., Dumont, M. (1986), Int. J. Peptide Protein Res., 27, 300-305; Gairin, J.E., Gouarderes, C., Mazarguil, H., Alvinerie, P., Cros, J. (1984) Eur. J. Pharmacol., 106, 457-458; Gairin, J.E., Gout, R., Meunier, J.-C., and Cros, J. (1988), J. Pharmacol. Exp. Ther., 245, 995-1001).

Thus far, the most potent and selective kappa opioid receptor agonists have been several non-peptide analogs of N-methyl-N-[(pyrrolidinyl)-cyclohexyl]benzeneacetamide. FIG. 1 shows the structures of U-50488 and related analogs. The analog U-50488 is a racemic mixture while U-69593 is enantiomerically pure. U-50488 and its analogs do not display morphine-type physical dependence, urogenic activity or respiratory depression and appear to prevent the development of tolerance to morphine analgesia. However, use of these compounds is disadvantageous in that they induce tolerance, cause water diuresis and have been implicated in the production of psychotomimesis.

The most potent and selective peptidic opioid receptor agonist which has been reported is [D-pro$^{10}$]Dyn A$_{1-11}$-OH (DPDYN). See Gairin et al., Eur. J. Pharmacol., loc. cit. DPDYN exhibits high $\kappa$ vs. $\mu$ and $\kappa$ vs $\delta$ selectivities with a reported binding affinity of about 0.032 nM against the kappa ligand [$^3$H]Bremazocine. When administered i.c.v., DPDYN did not show any activity against thermal stimulus but, in contrast, produced a dose-related effect against chemical pain (Gairin et al., J. Pharmacol. Exp. Ther. loc. cit.).

Attempts have been made to investigate the secondary structure of Dyn-A using various spectroscopic methods. Infrared attenuated total reflection spectroscopy and capacitance minimization have been used to study the secondary structure, orientation and accumulation of DYN A$_{1-13}$ molecules on the surface of planar phosphocholine derived membranes (D. Erne, et al. (1985) Biochemistry, 24:4161–4263). Erne et al. proposed that the peptide assumes a helical structure extending from Tyr[1] to Pro[10] oriented perpendicularly to the membrane surface, while the remaining C-terminal residues adopt a random coil conformation.

To study the aqueous phase secondary structure of Dyn $A_{1-13}$, FT-infrared spectroscopic studies in $H_2O$ and $D_2$ were utilized in conjunction with proton NMR deuterium exchange studies (V. Renugopalakrishnan et al., (1988), Biochem. Biophys. Res. Commun., 151:1220–1225). The peptide NH groups appeared to be solvent accessible which was suggestive of an essentially extended structure with a periodically interwoven unordered structure. These results are consistent with previous Raman spectroscopic experiments (Rapaka, R.S., Renugopalakrishnan,. V., Collete, T.W., Dobbs, J.C., Carreira, L.A., and Bhatnagar, R.S. (1987), Int. J. Peptide Protein Res., 30, 284–287; 2D-NOESY spectra (Renugopalakrishnan, V., Rapaka, R.S., Huang, S.-G., Moore, S. and Hutson, T.B. (1988), Biochem. Biophys. Res. Commun., 151, 1220–1225) and extensive 1D and 2D NMR studies (Zhou, N. and Gibbons, W.A. (1986), J. Chem. Soc. Perkin Trans. II, 637–644). Additional spectroscopic experiments supporting the existence of an extended and/or random conformation of Dyn A in an aqueous environment include fluorescence energy transfer studies (Schiller, P.W., (1983), Int. J. Peptide Protein Res., 21, 307–312) and circular dichroism studies (Kojro, E., Gwizdala, E., Grzonka, Z. (1987), Polish J. Chemistry, 61, 415–424).

Additionally, the secondary structure of dynorphin oligopeptides has been studied through the use of conformationally constrained analogs. The first conformationally constrained dynorphin A analog reported was the cyclic disulfide

[D-Cys$^2$, Cys$^5$]Dyn $A_{1-13}$ (Schiller, P.W., Eggiman, B., and Nguyen, T.M.-D, (1982), Life Sci., 31, 1777–1780). This compound exhibits high biological activity and a high affinity for the mu receptor. Cyclic lactams of Dyn A such as

[D-Orn$^2$, Asp$^5$]Dyn $A_{1-8}$, [Orn$^5$, Asp$^8$]Dyn $A_{1-13}$,

[Orn$^5$, Asp$^{10}$]Dyn $A_{1-13}$ and [Orn$^5$, Asp$^{13}$]Dyn $A_{1-13}$ have also been prepared (Schiller, P.W., Nguyen, T.M.-D., Lemieux, C. (1988), Tetrahedron, 44, 733–743). These cyclic lactams show varying degrees of biological activity but generally low or negligable interaction with the kappa receptor. It has generally been concluded that these cyclic lactams of Dyn A do not have kappa selectivity.

A continuing need exists for new oligopeptides with improved receptor selectivity enhanced biological activity, and selectivity for the brain or peripheral kappa receptor sites.

SUMMARY OF THE INVENTION

Accordingly, one object of the invention is to provide oligopeptides having receptor selectivity and high biological activity.

A further object is an oligopeptide having high kappa receptor selectivity, high biological activity, and high selectivity for central vs. peripheral kappa opioid receptors.

These and other objects which will become apparent from the following specification have been achieved by the present cyclic and linear dynorphin A analogs. The cyclic analogs of the present invention are analogs of Dyn $A_{1-11}$ and Dyn $A_{1-13}$ having a cyclic disulfide structure or a linear structure with unexpected activities. These analogs exhibit selective binding affinities for the kappa receptor, apparent specificity for central vs. peripheral kappa receptor and exhibit good biological activity such as those related to an opioid response in the guinea pig ileum (GPI) bioassay or in other assays for opioid activity.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
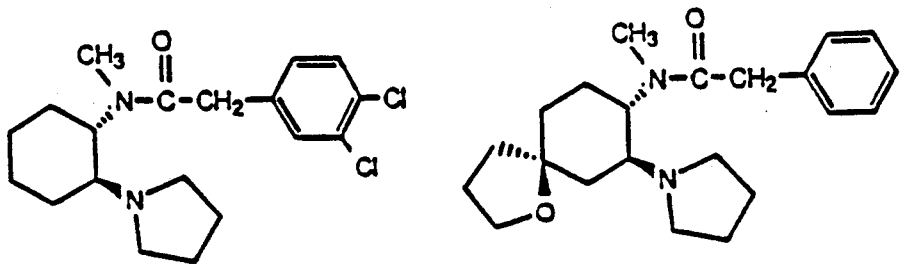
FIG. 1 shows known non-peptide kappa receptor agonists.
Figure 1:
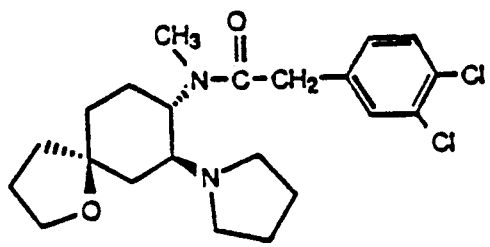
Figure 2:
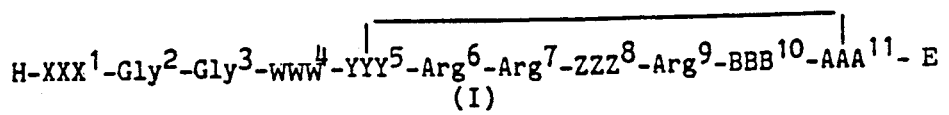
FIG. 2 shows the general structure for the cyclic and linear dynorphin A analogs of the present invention.
Figure 2:
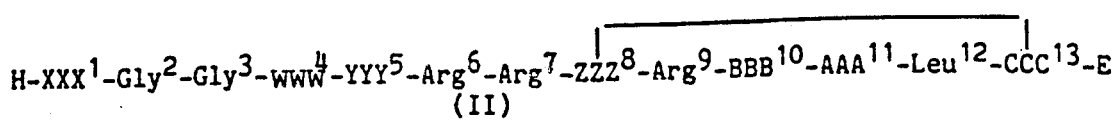
Figure 2:
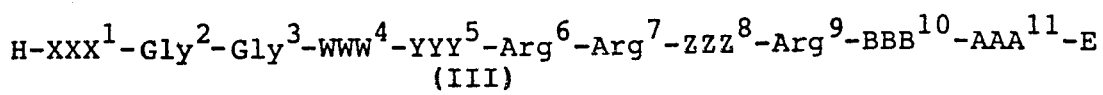

The cyclic dynorphin A analogs of the present invention are conformationally restricted by the presence of a cyclic disulfide ring system. Analog I has 11 amino acids and a cyclic disulfide ring between amino acids 5 and 11. Analog II contains 13 amino acids and contains a cyclic disulfide ring between amino acids 8 and 13. Analogs I and II are closely related structurally.

Cyclic dynorphin analogs I and II have the structures shown below.

H—XXX$^1$—Gly$^2$—Gly$^3$—WWW$^4$—YYY$^5$—Arg$^6$—Arg$^7$—ZZZ$^8$—Arg$^9$—BBB$^{10}$—AAA$^{11}$—E (I)

H—XXX$^1$—Gly$^2$—Gly$^3$—WWW$^4$—YYY$^5$—Arg$^6$—Arg$^7$—ZZZ$^8$—Arg$^9$—BBB$^{10}$—AAA$^{11}$—Leu$^{12}$—CCC$^{13}$—E (II)

Linear dynorphin analog III has the following structure:

H-XXX$^1$-Gly$^2$-Gly$^3$-WWW$^4$-YYY$^5$-Arg$^6$-Arg$^7$-ZZZ$^8$-Arg$^9$-BBB$^{10}$-AAA$^{11}$-E (III)

In analogs I, II and III, the first amino acid XXX$^1$ is a D- or L- aromatic amino acid. The aromatic amino acid may be unsubstituted such as D- or L-tyrosine, phenylalanine or tryptophan, for example, or may be an aromatic amino acid in which the aromatic ring is substituted with a halogen such as F, Cl, Br, or I, a nitro, a cyano, or a $C_{1-6}$, preferably $C_{1-4}$ alkyl group in the ortho, meta or para position. The aromatic amino acid preferably contains a single substituent, but may contain more than one substituent on the aromatic ring. Preferred unsubstituted and ring substituted aromatic amino acids include L-Tyr, D-Tyr, L-Phe, D-Phe, Tic (tetrahydroisoquinoline-3-carboxylate), p-$NO_2$-Phe, p-F-Phe, p-Cl-Phe, p-Br-Phe, p-I-Phe and p-Cl-Phe. Additionally, the amino acid $XXX^1$ may be a $\beta$-alkyl amino acid derivative in which one or both of the $\beta$ hydrogen atoms is replaced with a $C_{1-6}$ alkyl group. Preferred examples include $\beta$-Me-Phe and $\beta$-Me-Tyr.

In analogs I, II and III, amino acid $WWW^4$ is D- or L-Phe, D- or L-Tic, or other D- or L-aromatic or aliphatic amino acids such as Tyr, Trp, His or any aromatic amino acid in which the ortho, meta or para positions of the aromatic ring are substituted with groups such as F, Cl, Br, I, $NO_2$, $C_{1-6}$ (Me), CN, OH, etc.

In analog I, amino acid $YYY^5$ is D- or L-Cys, D- or L-homoCys, or D- or L-Pen (penicillamine) so as to form a disulfide ring with amino acid $AAA^{11}$. In analog II, $YYY^5$ is L-Leu or L-Met or the corresponding D-amino acids. In analog III, $YYY^5$ is a D- or L-aromatic or aliphatic amino acid such as Leu, Met, etc.

In analogs I and III, amino acid $ZZZ^8$ is L-Ile, L-Val, L-Nle, L-Leu or D-Ala. In analog II, amino acid $ZZZ^8$ is D- or L-Cys or D- or L-homoCys and forms a disulfide ring with amino acid $CCC^{13}$.

Amino acid $BBB^{10}$ may be L-Pro, D-Pro or L-Sar or D-Sar (sarcosine) in analogs I, II or III.

In analog I, amino acid $AAA^{11}$ is D- or L-Cys, D or L-homoCys or D- or L-Pen so as to form a disulfide ring with amino acid $YYY^5$. In analog II, amino acid $AAA^{11}$ is a basic amino acid such as L-Lys, L-Orn or L-Arg or the corresponding D-amino acids. In analog III, $AAA^{11}$ is also a basic amino acid.

In analog II, amino acid $CCC^{13}$ is D- or L-Cys, D-or L-homoCys or D- or L-Pen so as to form a disulfide ring with amino acid $ZZZ^8$.

[HomoCys$^5$, Cys$^{11}$]—, [homoCys$^5$, homoCys$^{11}$]—, and and the corresponding -DynA$_{1-13}$—NH$_2$ analogs may be cited as examples.

The carboxy terminal amino acid of analogs I, II and III may contain either a free carboxylic acid or a peptidase-stable carboxylic acid derivative (E). A preferred C-terminal group is the carboxamide group, methyl or other esters, or even carbinol (—CH$_2$OH) The amino terminal amino acid $XXX^1$ contains a free amino group, N-methyl or other N-alkyl, preferably $C_{1-6}$ alkyl amino groups.

The cyclic and linear peptides of the present invention may be synthesized using conventional solid-phase methods (see for example, Merrifield, R.B. (1963), J. Am. Chem. Soc., 85, 2149-2154) using an automated peptide synthesizer and conventional protecting group reagents or other conventional synthesis techniques. The oligopeptides produced can be purified using semi-preparative high pressure liquid chromatography (HPLC) or other conventional purification procedures. Disulfide ring formation is effected according to standard conventional procedures.

The dynorphin A analogs of the present invention exhibit improved kappa receptor selectivity and demonstrate high biological activity.

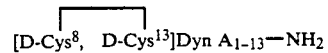
[D-Cys$^8$, D-Cys$^{13}$]Dyn A$_{1-13}$—NH$_2$ is selective and potent in the GPI bioassay and a full agonist in vivo (icv, analgesia A$_{50}$=10$\mu$g).

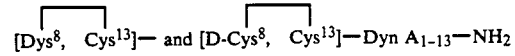
[Dys$^8$, Cys$^{13}$]— and [D-Cys$^8$, Cys$^{13}$]—Dyn A$_{1-13}$—NH$_2$ are also potent but not as selective in the GPI.

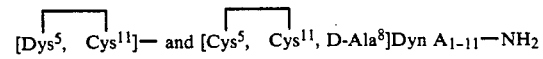
[Dys$^5$, Cys$^{11}$]— and [Cys$^5$, Cys$^{11}$, D-Ala$^8$]Dyn A$_{1-11}$—NH$_2$ have high affinities for $\kappa$ and $\mu$ receptors in binding assays and hence are only selective against $\delta$; however both show weak activities (1080 and 4400 nM respectively) in the GPI assay. Thus they have high central vs. peripheral selectivities.

Other features of the invention will become apparent during the course of the following descriptions of exemplary embodiments which are given for illustration of the invention and are not intended to be limiting thereof.

EXAMPLES

Peptide synthesis and purification

Peptide syntheses were performed via the solid-phase method (Merrifield, R.B., (1963), J. Am. Chem. Soc., 85, 2149-2154) utilizing an automated synthesizer (Applied Biosystems Inc. Model 431A, Applied Protein Tech. Model PSS-80, or Vega Coupler Model 1000). Thin-layer chromatography (TLC) of synthetic peptides was performed on silica gel plates (0.25 mm, Analtech, Newark, DE) with the following solvent systems 1-butanol/pyridine/acetic acid/water (15/10/3/8, v/v/v/v), 1-butanol/pyridine/acetic acid/water (6/6/1/5, v/v/v/v), 1-butanol/acetic acid/water (4/1/5, v/v/v), and isopropanol/conc. ammonium hydroxide/water (3/10/10, v/v/v). Peptides were detected with ninhydrin reagent. Para-methylbenzhydrylamine resin was purchased from Advanced Chem. Tech. (Louisville, KY), or U.S. Biochemical Corp. (Cleveland, OH). N-$\alpha$-Boc-amino acids (N-$\alpha$-Boc- O-(2,6-dichlorobenzyl)tyrosine, N-$\alpha$-Boc-N-$\epsilon$-(2,4-dichlorobenzyloxycarbonyl)lysine, N-$\alpha$- Boc-N-G-tosyl arginine) were purchased from Bachem Inc., Torance, CA, or were synthesized by standard methods. Hydrolysis of the peptides was performed in 4N methanesulfonic acid (0.2% 3-(2-aminoethyl)indole) at 110° C. for 24 h and amino acids were analyzed with an automatic analyzer (Model 7300, Beckman Instruments) Mass spectra (fast-atom bombardment, low-resolution full scan, glycerol or dithioerythritol/dithiothreitol matrix) were performed using standard procedures. HPLC was carried out by use of a ternary pump (Spectra Physics Model 8800) equipped with a UV/VIS detector (Spectra Physics 8450) and integrator (Spectra Physics 4270). For analytical HPLC the solvent system used was binary system, water containing 0.1% trifluoroacetic acid (TFA), (pH 2.0) and acetonitrile as the organic modifier, and solvent programs involved linear gradients as follows: 1) 13% to 33% acetonitrile over 20 min with flow rate of 1.5 mL/min; 2) 10% to 30% acetonitrile over 20 min with flow rate of 2.0 mL/min; 3) 15% to 30% acetonitrile over 15 min with flow rate of 2.0 mL/min; 4) 10% to 30% acetonitrile over 20 min with flow rate of 1.5 mL/min, and 5) 15% acetonitrile isocratically over 10 min followed by 15% to 45% acetonitrile over 60 min. The column used for analytical chromatography had dimensions of 4.5×250 mm (Vydac, 10 μm particle size, C-18). HPLC purification on a semi-preparative scale (10 mg) was performed with a reverse phase column (Vydac, 1.0×25 cm, C-18, 10 μm particle size) employing the same binary solvent system used for analytical HPLC. Preparative (100 mg) low pressure (50 psi) chromatographic purification was accomplished with a reversed-phase glass column (Bio-Rex column, 2.5×48 cm, Vydac C-18 resin, 30 μm particle size). A linear gradient of 0% to 30% acetonitrile over 3 h, involving the mentioned binary solvent system, was routinely used with a flow rate of 2 mL/min. Dyn $A_{1-11}$-$NH_2$ and Dyn $A_{1-13}$-$NH_2$ were synthesized and purified using procedures as described for Dyn $A_{1-11}$-$NH_2$

EXAMPLE 1 —Protected Dyn $A_{1-11}$-$NH_2$-resin

Para-methylbenzhydrylamine resin (1.06g, 0.5 mequiv) was esterified with N-α-Boc-N-ε-(2,4-dichlorobenzyloxycarbonyl)lysine via its N-hydroxybenzotriazole (HOBt) active ester (Stewart, J.M.; Young, J.D. Solid Phase Peptide Synthesis, second edition, 1984, Pierce Chemical Co., Rockford, IL, page 82). N-a-Boc-amino acids (4 mequiv) were added to the reaction mixture as preformed HOBt activated esters. DMF or N-methyl-2-pyrrolidinone were used as reaction solvent, and the coupling reaction times were normally 30-60 min. Diisopropylethylamine was utilized as base and dichloromethane or DMF was used as solvents for washes. Side-chain protection was as follows: Lys:2,4-dichlorobenzyloxycarbonyl; Arg:tosyl; Tyr:2,6-dichlorobenzyl; and Cys:para-methylbenzyl. After deprotection of the last N-α-Boc group with 50% trifluoroacetic acid (TFA) in dichloromethane, the peptide-resin was dried in vacuo to yield the protected Dyn $A_{1-11}$-$NH_2$-resin.

EXAMPLE 2 —Dyn $A_{1-11}$-$NH_2$

The protected peptide-resin was treated with liquid anhydrous hydrofluoric acid (HF) in the presence of anisole (10%, v/v) for 1h at −10-0° C. After removal of HF in vacuo at 0° C., the residue was washed three times with ether and extracted with aqueous 6% acetic acid three times. The acetic acid solution was lyophilized to give a yellow solid (0.40 g) which was dissolved in 30% acetic acid and subjected to gel-filtration (Sephadex G-15) with 30% acetic acid as eluant. A cream power (0.385 g) was obtained after gel-filtration and this product was subjected to preparative HPLC under the mentioned conditions to yield a white powder (212 mg) after lyophilization. The structure assignment was corroborated by the results of the amino acid analysis (Table 1) and mass spectrometry (Table 2), and the purity of the product was characterized by analytical HPLC and TLC (Table 2).

EXAMPLE 3

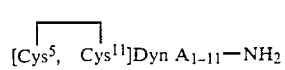
(1)

The crude deprotected peptide was obtained as a white powder (273 mg) by the use of procedures as described for Dyn $A_{1-11}$-$NH_2$ After dissolving the crude product in degassed aqueous 0.1% acetic acid, the solution was diluted to a volume of 2 liters with degassed deionized distilled water. The pH was adjusted to 8.5 by the addition of 3N ammonium hydroxide and 0.01 N $K_3Fe(CN)_6$ (15 mL) was added dropwise to a yellow endpoint. Additional 0.01 N $K_3Fe(CN)_6$ (19 mL) was added and the mixture was stirred at room temperature for 60 min after which time the solution remained a yellow color The pH was adjusted to 4 by the addition of 30% acetic acid and anion exchange resin (Amberlite IRA-68, chloride form, 50 mL) was added to the solution. After stirring the mixture for 60 min, the solution was colorless. The resin was filtered and washed three times with 30% acetic acid, and the solvent was evaporated at 40-45° C. to a volume of about 100 mL. Lyophilization of this solution yielded a pale-green powder which was subjected to preparative HPLC as described to give a white powder (92 mg). The purity of the final product was verified by TLC and analytical HPLC (Table 2), and the structure assignment was corroborated by the amino acid analysis (Table 1) and mass spectrum (FAB) (Table 2) results. In addition a quantitative Ellman test (Stewart, J.M.; Young, J.D. Solid Phase Peptide Synthesis, second edition, 1984, Pierce Chemical Co., Rockford, IL, page 116) was performed, with oxytoceine as standard, to verify the absence of free sulfhydryl groups.

EXAMPLE 4

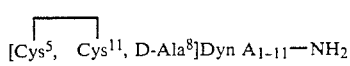
(2)

Compound 2 was synthesized and purified in a manner similar to that employed for compound 1. After purification, the final product was obtained as a white powder (61 mg). The purity of the final product was verified by TLC and analytical HPLC (Table 2), and the structure assignment was corroborated by the amino acid analysis (Table 1) and mass spectrum (FAB) (Table 2) results.

EXAMPLE 5

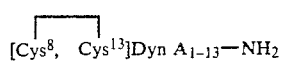
(3)

Compound 3 was synthesized and purified in a manner similar to that employed for compound 1. After purification, the final product was obtained as a white powder (64 mg). The purity of the final product was verified by TLC and analytical HPLC (Table 2), and the structure assignment was corroborated by the amino acid analysis (Table 1) and mass spectrum (FAB) (Table 2) results.

EXAMPLE 6

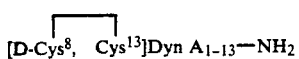
[D-Cys$^8$, Cys$^{13}$]Dyn A$_{1-13}$—NH$_2$ (4)

Compound 4 was synthesized and purified in a manner similar to that employed for compound 1. After purification, the final product was obtained as a white powder (43 mg). The purity of the final product was verified by TLC and analytical HPLC (Table 2), and the structure assignment was corroborated by the amino acid analysis (Table 1) and mass spectrum (FAB) (Table 2) results.

EXAMPLE 7

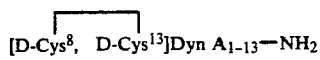
[D-Cys$^8$, D-Cys$^{13}$]Dyn A$_{1-13}$—NH$_2$ (5)

Compound 5 was synthesized and purified in a manner similar to that employed for compound 1. After purification, the final product was obtained as a white powder (43 mg). The purity of the final product was verified by TLC and analytical HPLC (Table 2), and the structure assignment was corroborated by the amino acid analysis (Table 1) and mass spectrum (FAB) (Table 2) results.

EXAMPLE 8

[para-Bromo-Phe$^1$, D-Ala$^8$]Dyn A$_{1-11}$—NH$_2$ (6)

The title compound was synthesized and purified in a manner similar to that employed for Dyn A$_{1-11}$-NH$_2$. After purification, the final product was obtained as a white powder (191 mg). The purity of the final product was verified by TLC and analytical HPLC (Table 2), and the structure assignment was corroborated by the amino acid analysis (Table 1) and mass spectrum (FAB) (Table 2) results.

EXAMPLE 9

The title compound was synthesized and purified in a manner similar to that employed for Dyn A$_{1-11}$-NH$_2$ except that the synthesis was performed on a 0.25 mmol scale. After purification, the final product was obtained as white powder (54 mg). The purity of the final product was verified by TLC and analytical HPLC (Table 2), and the structure assignment was corroborated by the amino acid analysis (Table 1) and mass spectrum (FAB) (Table 2) results.

In vitro bioassays

The known guinea pig ileum (GPI) longitudinal muscle/myenteric plexus preparation was used for in vitro bioassays (Kosterlitz, H.W., Lydon, R.J., and Watt, A.J., (1970), Br. J. Pharmacol., 39, 398–413). The tissues were suspended under a final tension of 1 g in organ baths, bathed with Krebs buffer (NaCl 118 mM, KCl 4.7 mM, CaCl$_2$ 2.5 mM, KH$_2$PO$_4$ 1.19 mM, MgSO$_4$ 1.18 mM, NaHCO$_3$ 25 mM, and glucose 11.48 mM), maintained at 37° C. and aerated with 95% O$_2$/5% CO$_2$. Electrical stimuli were 0.4 msec pulses of supramaximal voltage, at a rate 6/min. Isometric contractions were measured via strain gauge force transducers on chart recorders. The mouse vas deferens (MVD) preparation was also performed as described by Hughes et al. (Hughes, J., Kosterlitz, H.W., and Leslie, F.M., (1975), Br. J. Pharmacol., 53, 371–381). The Krebs buffer was made as above, but without magnesium and the tissues were suspended under a final tension of 500 mg. Pulse duration was 2 msec. Dose-response testing in all preparations was carried out in a cumulative fashion. The compounds were tested for intrinsic agonist activity in the two in vitro bioassays. Thus, concentrations showing intrinsic activity for each analog were tested in the presence of naloxone (1000 nM) to define opioid activity. To further define the opioid selectivity of the agonist effect, the δ selective antagonist ICI 174,864 (Cotton, R., Giles, M.G., Miller, L., Shaw, J.S., and Timms, D. (1984), Eur. J. Pharmacol., 97, 331-332) was utilized in the MVD, and the μ selective antagonists CTAP (Pelton, J.T., Kazmierski, W., Gulya, K., Yamamura, H.I., and Hruby, V.J. (1986), J. Med. Chem., 29, 2370-2375) or CTP (Pelton, J.T., Gulya, K., Hruby, V.J., Duckles, S., and Yamamura, H.I. (1985) Proc. Natl. Acad. Sci. U.S.A., 82, 236-239) were employed in the GPI, all at 1000 nM. K$_e$ values were calculated according to the formula:

$$K_e = [Ant]/[DR-1]$$

where [Ant] is the concentration of the antagonist, and DR is the dose ratio (i.e., IC$_{50}$ after antagonism divided by the IC$_{50}$ before antagonist activity was measured).

Radioligand binding assay

The binding affinities of the analogues at κ opioid receptors were determined by inhibition of 1.0 nM [$^3$H]U-69593 (42.1 Ci/mmole, New England Nuclear) binding to whole guinea pig brain membrane assayed in 50 mM Tris-HCl buffer at pH 7.4 containing 1.0 mg/mL bovine serum albumin, 50 μg/mL bacitracin, 30 μM bestatin, 10 μM captopril and 1.0 mM phenylmethylsulfonyl fluoride to a final volume of 1.0 mL. Samples were incubated for 1.0 h at 25° C. before filtration through glass fiber filter strips (GF/B, Whatman) pretreated with 0.1% polyethylenimine. Nonspecific binding (=20% of total binding) was defined as binding measured in the presence of 1.0 μM Dyn A$_{1-13}$. The affinities of the analogues for [$^3$H]Tyn—Pro—N—Me—Phe—D—Pro—NH$_2$, (84.2 Ci/mmole, New England Nuclear) and 1.0 nM [$^3$HDPDPE, i.e.,

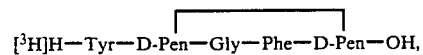
[$^3$H]H—Tyr—D-Pen—Gly—Phe—D-Pen—OH, (33.6 Ci/mmole, New England Nuclear), respectively. Inhibition was measured using membranes prepared from whole rat brain (less cerebellum) as previously described (Hawkins, K.N., Knapp, R.J., Lui, G.K., Gulya, K., Kazmierski, W., Wan, Y.-P., Pelton, J.T., Hruby, V.J., and Yamamura, H.I. (1988), J. Pharmacol. Exp. Ther., 248, 73-80).

Competitive binding experiments for the cyclic dynorphin A analogs of the present invention and known dynorphin oligopeptides with rat (μ and δ) and guinea pig (κ) brain homogenates are shown in Table 3. Smooth muscle bioassays utilizing the guinea pig ileum and mouse vas deferens are shown in Table 4.

The compounds of the present invention exhibit surprising selectivity for the κ receptor relative to other dynorphin oligopeptides. This high selectivity for the κ receptor enables one to produce pharmaceutical compositions having selective pharmacological activities. Additionally, the high κ receptor selectivity will be useful in the further elaboration and identification of opioid receptors and the conformations of opioid receptor oligopeptide ligands.

Obviously, numerous modifications and variations of the present invention are possible in light of the above teachings. It is therefore to be understood that within the scope of the appended claims, the invention may be practiced otherwise than as specifically described herein.

TABLE 1

| no | compound | Pro | Gly | Ala | Ile | Leu | Tyr | Phe | Lys | Arg | Cys |
|----|----------|-----|-----|-----|-----|-----|-----|-----|-----|-----|-----|
| 1 | [Cys$^5$, Cys$^{11}$]Dyn A$_{1-11}$—NH$_2$ | 1.1(1)$^a$ | 2.02(2) | | 0.98(1) | | 0.91(1) | 1.0(1) | | 3.1(3) | 2.2(2) |
| 2 | [Cys$^5$, Cys$^{11}$]D-Ala$^8$]Dyn A$_{1-11}$—NH$_2$ | 1.1(1) | 2.0(2) | 1.1(1) | | | 1.0(1) | 1.0(1) | | 3.1(3) | 2.0(2) |
| 3 | [Cys$^8$, Cys$^{13}$]Dyn A$_{1-13}$—NH$_2$ | 1.0(1) | 2.0(2) | | | 2.0(2) | 0.91(1) | 0.90(1) | 0.98(1) | 2.9(3) | 2.0(2) |
| 4 | [D-Cys$^8$, Cys$^{13}$]Dyn A$_{1-13}$—NH$_2$ | 1.1(1) | 2.0(2) | | | 1.9(2) | 1.0(1) | 0.92(1) | 1.0(1) | 2.9(3) | 2.0(2) |
| 5 | [D-Cys$^8$, D-Cys$^{13}$]Dyn A$_{1-13}$—NH$_2$ | 1.0(1) | 2.0(2) | | | 2.0(2) | 0.96(1) | 0.93(1) | 0.98(1) | 2.8(3) | 2.0(2) |
| 6 | [Phe$^1$, D-Pro$^{10}$]Dyn A$_{1-11}$—NH$_2$ | 1.0(1) | 2.0(2) | | | 0.90(1) | 0.98(1) | 2.0(2) | 1.1(1) | 2.9(3) | |
| 7 | [p-BrPhe$^1$, D-Ala$^8$]Dyn A$_{1-11}$—NH$_2$ | 0.95(1) | 2.1(2) | 1.1(1) | | 0.99(1) | | 0.98(1) | 1.0(1) | 3.0(3) | |

$^a$Theoretical values in parenthesis. Hydrolysis in 4N methanesulfonic acid (0.2% 3-(2-aminoethyl)indole) at 110° C. for 24 h.

TABLE 2

Analytical characteristics of cyclic Dynorphin A analogues

| Compound | Thin-layer R$_f$ Values | | Chromatography | | HPLC K' Values | FAB-MS$^a$ |
|----------|------|------|------|------|------|------|
| | I | II | III | IV | | |
| 1 | 0.63 | 0.70 | 0.17 | 0.83 | 2.93$^1$ | 1325[M + H]$^+$ |
| 2 | 0.58 | 0.70 | 0.15 | 0.83 | 2.84$^2$ | 1283[M + H]$^+$ |
| 3 | 0.56 | 0.72 | 0.07 | 0.75 | 4.87$^2$ | 1565[M]$^+$ |
| | | | | | | 1566[M + H]$^+$ |
| 4 | 0.62 | 0.70 | 0.10 | 0.77 | 3.08$^3$ | 1565[M]$^+$ |
| 5 | 0.62 | 0.70 | 0.12 | 0.71 | 5.18$^4$ | 1567[M + 2H]$^+$ |
| 6 | 0.55 | — | — | — | 15.4$^5$ | 1346[M + H]$^+$ |
| 7 | 0.57 | — | — | — | 4.37$^3$ | 1382,1384[M + H]$^+$ |

I: 1-Butanol/pyridine/acetic acid/water (15/10/3/8, v/v/v/v).
II: 1-Butanol/acetic acid/water (4/1/5, v/v/v).
III: isopropanol/conc. ammonium hydroxide/water (3/10/10, v/v/v).
IV: 1-Butanol/pyridine/acetic acid/water (6/6/1/5, v/v/v/v).
$^a$Fast-atom bombardment, low-resolution full scan, glycerol or DTE/DTT matrix.
$^{1-5}$See Experimental Section for HPLC solvent systems and solvent programs used.

TABLE 3

Opioid receptor binding affinities and selectivities of various cyclic disulfide Dynorphin analogues with rat and guinea pig brain homogenate.$^a$

| no. | Compound | IC$_{50}$ (nM) [$^3$H]-U-69,593 | [$^3$H]PL17* | [$^3$H]-DPDPE | μ/κ | δ/κ |
|-----|----------|------|------|------|-----|-----|
| | Dyn A$_{1-11}$—NH$_2$ | 0.077 ± 0.017 | 1.01$^+$ | 6.09 | 13 | 79 |
| | Dyn A$_{1-13}$—NH$_2$ | 0.109 ± 0.003 | 1.33$^+$ | 2.96 | 12 | 27 |
| 1 | [Cys$^5$, Cys$^{11}$]Dyn A$_{1-11}$—NH$_2$ | 0.39 ± 0.06 | 2.3 ± 0.72 | 18.6 ± 7.50 | 6 | 48 |
| 2 | [Cys$^5$, Cys$^{11}$]D-Ala$^8$]Dyn A$_{1-11}$—NH$_2$ | 0.28 ± 0.036 | 0.27 ± 0.14 | 1.63 ± 0.53 | 1 | 6 |
| 3 | [Cys$^8$, Cys$^{13}$]Dyn A$_{1-13}$—NH$_2$ | 0.074 ± 0.031 | 0.98 ± 0.12 | 3.97 ± 0.96 | 13 | 54 |
| 4 | [D-Cys$^8$, Cys$^{13}$]Dyn A$_{1-13}$—NH$_2$ | 1.76 ± 0.35 | 10.3 ± 3.9 | 104 ± 1.86 | 6 | 59 |
| 5 | [D-Cys$^8$, D-Cys$^{13}$]Dyn A$_{1-13}$—NH$_2$ | 0.11 ± 0.009 | 0.36 ± 0.13 | 14.3 ± 1.86 | 3 | 130 |
| 6 | [Phe$^1$, D-Pro$^{10}$]Dyn A$_{1-11}$—NH$_2$ | 2.4 ± 0.56 | 120 ± 22 | 390 ± 52 | 50 | 163 |

TABLE 3-continued

Opioid receptor binding affinities and selectivities of various cyclic disulfide Dynorphin analogues with rat and guinea pig brain homogenate.[a]

| no. | Compound | IC$_{50}$ (nM) [$^3$H]-U-69,593 | [$^3$H]PL17* | [$^3$H]-DPDPE | μ/κ | δ/κ |
|---|---|---|---|---|---|---|
| 7 | [p-BrPhe$^1$, D-Ala$^8$]Dyn A$_{1-11}$—NH$_2$ | 1.7 ± 0.14 | 47 ± 5.1 | 1060 ± 40 | 28 | 624 |

[a]Binding experiments for the κ, μ and δ opioid receptors was performed with guinea pig brain homogenate
*[$^3$H]H—Tyr—Pro—N—MePhe—D-Pro—NH$_2$
+1 assay
2 assays

TABLE 4

Bioassays with the smooth muscle tissue of the guinea pig ileum and the mouse vas deferens

| no. | Compound | Bioassay | IC$_{50}$ (nM) | K$_e$ (nM) for: NLX | CTAP | ICI |
|---|---|---|---|---|---|---|
|  | Dyn A$_{1-17}$—OH | GPI | 2.5 | 66.7 | no* | nd |
|  |  | MVD | 22.5 | 58.8 | no* | no |
|  | Dyn A$_{1-11}$—NH$_2$ | GPI | 7.5 | r | nr* | nd |
|  |  | MVD | 204 | 125 | no* | 625 |
|  | Dyn A$_{1-13}$—NH$_2$ | GPI | 1.7 | 82 | 2000 | nd |
|  |  | MVD | 7.8 | 100 | no | nd |
| 1 | [Cys$^5$, Cys$^{11}$]Dyn A$_{1-11}$—NH$_2$ | GPI | 1080 | 66.7 | no | nd |
|  |  | MVD | 421 | 80 | 2000 | 86.2 |
| 2 | [Cys$^5$, Cys$^{11}$, D-Ala$^8$]Dyn A$_{1-11}$NH$_2$ | GPI | 4406 | y | 50 | nd |
|  |  | MVD | 1660 | nd | 500 | 21.3 |
| 3 | [Cys$^8$, Cys$^{13}$]Dyn A$_{1-13}$—NH$_2$ | GPI | 1.3 | 38.9 | no | nd |
|  |  | MVD | 20.1 | 95.2 | 175 | 156 |
| 4 | [D-Cys$^8$, Cys$^{13}$]Dyn A$_{1-13}$—NH$_2$ | GPI | 2.27 | 32.3 | 256 | nd |
|  |  | MVD | 24.5 | 35.6 | 370 | 667 |
| 5 | [D-Cys$^8$, D-Cys$^{13}$]Dyn A$_{1-13}$—NH$_2$ | GPI | 1.75 | 233 | no | nd |
|  |  | MVD | 19.5 | 18.2 | 1430 | 1000 | r = reversed a high concentration, antagonist study of entire dose-response curve (drc) not completed.
nr = did not reverse a high concentration.
y = shifted drc.
no = did not shift drc
* = CTP, not CTAP used as mμ antagonist.
nd = not determined.

What is new and desired to be secured by letters patent of the United States is:

1. A cyclic or linear dynorphin having structure I, II or III shown below,

H—XXX$^1$—Gly$^2$—Gly$^3$—WWW$^4$— (I)

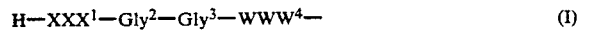
—YYY$^5$—Arg$^6$—Arg$^7$—ZZZ$^8$—Arg$^9$—BBB$^{10}$—AAA$^{11}$—E

H—XXX$^1$—Gly$^2$—Gly$^3$—WWW$^4$—YYY$^5$—Arg$^6$— (II)

—Arg$^7$—ZZZ$^8$—Arg$^9$—BBB$^{10}$—AAA$^{11}$—Leu$^{12}$—CCC$^{13}$—E H-XXX$^1$-Gly$^2$-Gly$^3$-WWW$^4$-YYY$^5$-Arg$^6$-Arg$^7$-ZZZ$^8$-Arg$^9$-BBB$^{10}$-AAA$^{11}$-E (III)

wherein in structure I, XXX$^1$ is a D or L-aromatic amino acid or a halogen, nitro, cyano or C$_{1-6}$ alkyl ring-substituted aromatic amino acid, YYY$^5$ is D-Cys, L-Cys, D-homoCys, L-homoCys, D-Pen or L-Pen; WWW$^4$ is a Dnitro, or L-aromatic or aliphatic amino acid or a halogen, cyano, hydroxy, or C$_{1-6}$ alkyl ring substituted aromatic amino acid; ZZZ$^8$ is L-Ile, L-Val, L-Nle, L-Leu or D-Ala, BBB$^{10}$ is L-Pro, D-Pro, L-Sar or D-Sar and AAA$^{11}$ is D-Cys, L-Cys, D-homoCys, L-homoCys D-Pen or L-Pen, wherein the thiol groups of amino acids YYY$^5$ and AAA$^{11}$ are bonded together so as to form a disulfide ring;

in structure II, XXX$^1$ is as defined above, YYY$^5$ is D-Leu, L-Leu, D-Met or L-Met; WWW$^4$ is a D— or L-aromatic or aliphatic amino acid or a halogen, nitro, cyano, hydroxy, or C$_{1-6}$ alkyl ring substituted aromatic amino acid; ZZZ$^8$ is D-Cys, L-Cys, D-homoCys or L-homoCys, BBB$^{10}$ is as defined above, AAA$^{11}$ is a basic amino acid and CCC13 is D-Cys, L-Cys, D-homoCys, L-homoCys, D-Pen or L-Pen, wherein the thiol groups of amino acids ZZZ$^8$ and CCC$^{13}$ are bonded together so as to form a disulfide ring; in structure III, XXX$^1$, WWW$^4$, ZZZ$^8$, and BBB$^{10}$ are as defined for structure I, YYY$^5$ is a D- or L-aliphatic or aromatic amino acid, and AAA$^{11}$ is a basic amino acid; and wherein E is a carboxylic acid or a peptidase-stable carboxylic acid derivative.

2. The cyclic dynorphin of claim 1, wherein E is a carboxamide group.

3. The cyclic dynorphin of claim 1, wherein said dynorphin has structure I.

4. The cyclic dynorphin of claim 3, wherein $XXX^1$ is an unsubstituted aromatic amino acid.

5. The cyclic dynorphin of claim 3, wherein $XXX^1$ is selected from the group consisting of L-Tyr, D-Tyr, L-Phe, D-Phe, Tic, p-F-Phe, p-Cl-Phe, p-Br-Phe, p-I-Phe, β-Me-Phe, p-NO$_2$-Phe and β-Me-Tyr.

6. The cyclic dynorphin of claim 3, wherein said dynorphin is selected from the group consisting of $[Cys^5, Cys^{11}]Dyn\ A_{1-11}-NH_2$ and $[Cys^5, Cys^{11}, D-Ala^8]Dyn\ A_{1-11}-NH_2$.

7. The cyclic dynorphin of claim 1, wherein said dynorphin has structure II.

8. The cyclic dynorphin of claim 7, wherein $XXX^1$ is an unsubstituted aromatic amino acid.

9. The cyclic dynorphin of claim 7, wherein $XXX^1$ is selected from the group consisting of L-Tyr, D-Tyr, L-Phe, D-Phe, Tic, p-F-Phe, p-Cl-Phe, p-Br-Phe, p-I-Phe, β-Me-Phe, p-NO$_2$-Phe and β-Me-Tyr.

10. The cyclic dynorphin of claim 8, wherein said dynorphin is selected from the group consisting of $[Cys^8, Cys^{13}]-Dyn\ A_{1-13}-NH_2$, $[D-Cys^8, Cys^{13}]Dyn\ A_{1-13}-NH_2$ and $[D-Cys^8, D-Cys^{13}]Dyn\ A_{1-13}-NH_2$.

11. The linear dynorphin of claim 1, wherein said dynorphin has structure III.

12. The linear dynorphin of claim 11, wherein $XXX^1$ is an unsubstituted aromatic amino acid.

13. The linear dynorphin of claim 11, wherein $XXX^1$ is selected from the group consisting of L-Tyr, D-Tyr, L-Phe, D-Phe, Tic, p-F-Phe, p-Cl-Phe, p-Br-Phe, p-I-Phe, β-Me-Phe, p-NO$_2$-Phe and β-Me-Tyr.

* * * * *